United States Patent [19]

Beck et al.

[11] Patent Number: 5,399,722

[45] Date of Patent: Mar. 21, 1995

[54] PROCESS FOR PREPARING TERT-BUTYL (3R,5S)-6-HYDROXY-3,5—O—ISOPROPYLIDENE-3,5-DIHYDROXYHEXANOATE

[75] Inventors: Gerhard Beck; Joachim-Heiner Jendralla, both of Frankfurt am Main; Kurt Kesseler, Bad Soden/Taunus, all of Germany

[73] Assignee: Hoechst Aktiengesellschaft, Frankfurt am Main, Germany

[21] Appl. No.: 83,488

[22] Filed: Jun. 30, 1993

[30] Foreign Application Priority Data

Jul. 2, 1992 [DE] Germany .................. 42 21 658.3

[51] Int. Cl.⁶ ............................................ C07D 319/06
[52] U.S. Cl. .................................... 549/375; 560/60
[58] Field of Search ........................... 549/375; 560/60

[56] References Cited

U.S. PATENT DOCUMENTS

| 4,452,994 | 6/1984 | Hill et al. | |
| 4,970,313 | 11/1990 | Wess et al. | 544/335 |
| 4,977,279 | 12/1990 | Wess et al. | 549/274 |

FOREIGN PATENT DOCUMENTS

0319847A2  6/1989  European Pat. Off. .

OTHER PUBLICATIONS

"Steroselective Reduction of δ-Hydroxy-β-ketoesters", Kathawala et al., Helvetica Chimica Acta, 69:803–805 (1986).
"Homogeneous Asymmetric Hydrogenation of Functionalized Ketones", Kitamura et al., J. Am. Chem. Soc., 110:629–631 (1988).
"A Practical Asymmetric Synthesis of Carnitine", Kitamura et al., Tetrahedron Letters, 29 (13):1555–1556 (1988).
"Convenient Preparation of Binap-Ruthenium(II) Complexes Catalyzing Asymmetric Hydrogenation of Functionalized Ketones", Kitamura et al., Tetrahedron Letters, 32 (33):4163–4166 (1991).
"Synthesis and Biological Activity of New HMG–CoA Reductase Inhibitors. 3. Lactones of 6-Phenoxy-3,-5-dihydroxyhexanoic Acids", Journal of Medicinal Chemistry, 34 (10):2962–2983 (1991).
G. Wess et al. "Stereoselective Synthesis of HR780 a New Highly Potent HMG–CoA Reductase Inhibitor" Tetrahedron Letters, Bd. 31, Nr. 18, 1990, Oxford GB, pp. 2545–2548.
Manzocchi et al., "Studies on the Stereochemical Control of Fermenting Baker's Yeast Mediated Reductions: Some 3-and 4-Oxo Esters," J. Chem. Soc. Perkin Trans. 1, 1987, pp. 2753–2757.

Primary Examiner—Nicky Chan
Attorney, Agent, or Firm—Finnegan, Henderson, Farabow, Garrett & Dunner

[57] ABSTRACT

A novel process is described for preparing tert-butyl (3R, 5S ) 6-hydroxy-3,5-O-isopropylidene-3,5-dihydroxyhexanoate of the formula I

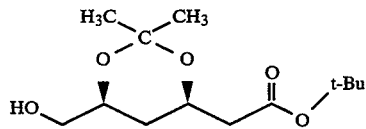

which is a valuable structural element for preparing inhibitors of HMG-CoA reductase.

2 Claims, No Drawings

PROCESS FOR PREPARING TERT-BUTYL (3R,5S)-6-HYDROXY-3,5—O—ISOPROPYLIDENE-3,5-DIHYDROXYHEXANOATE tert-Butyl (3R,5S)-6-hydroxy-3,5-O-isopropylidene-3,5-dihydroxyhexanoate of the formula I

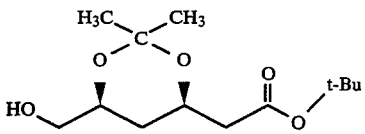

is a valuable structural element for preparing inhibitors of HMG-CoA reductase [EP-A-0319847 corresponding to U.S. Pat. Nos. 4,970,313 and 4,977,279; H. Jendralla et al., J. Med. Chem. 34, 2962 (1991) and earlier works cited therein, and German Patent Application P 4128345.7]. After oral administration, the latter lower the plasma cholesterol level in humans (M.J.T.M. Mol et al., Lancet 1986, 936) and thereby reduce the risk of coronary heart diseases [LRC-CPPT J. Am. Med. Assoc. 251, 351 and 365 (1984)].

A process for preparing the compound of the formula I, starting from (4S,6S)-7-benzyloxy-4,6-dihydroxyhept-1-ene, is proposed in German Patent Application P 41 28 345.7.

The preparation of the compound of the formula I, starting from L-malic acid, is described in EP-A-0319847. Via the route described, inhibitors of HMG-CoA reductase are readily accessible on a laboratory scale [see comparison of the synthetic pathways in J. Med. Chem. 34, 2962 (1991)]. However, on an enlarged industrial scale, this process, too, gives rise to problems. The main problem is the non-crystalline nature of all the intermediates and of the synthon of the formula I, in turn making several chromatographic purifications extremely necessary.

It has now been found that the compound of the formula I can be advantageously prepared from the economically priced ethyl ω-chloroacetoacetate or, with the elimination of one synthetic step, from the likewise commercially available ethyl ω-benzyloxyacetoacetate. The invention therefore relates to a process for preparing the compound of the formula I, wherein ethyl ω-benzyloxyacetoacetate of the formula II

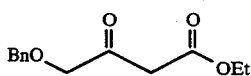

is asymmetrically hydrogenated to give ethyl 2(S)-hydroxy-3-benzyloxybutyrate of the formula III,

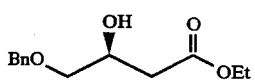

the β-hydroxy ester of the formula III is converted by means of a Claisen condensation into the β-keto-δ-(S)-hydroxy ester of the formula IV,

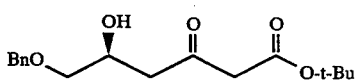

the resultant ester of the formula IV is converted by diastereoselective reduction into tert-butyl 3(R),5(S)-dihydroxy-6-benzyloxyhexanoate of the formula V,

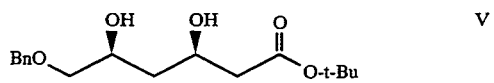

the hydroxyl groups in the dihydroxy ester of the formula V are protected, with the formation of the acetonide of the formula VI,

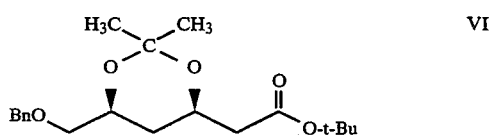

and the benzyl protective group is removed from the acetonide of the formula VI, with the formation of the compound of the formula I.

The compound of the formula II is commercially available or can be obtained in a known manner from ethyl ω-chloroacetoacetate. The principle of the process is evident from the following scheme:

Scheme:

synthesis of the lactone structural element of the formula I from ethyl ω-chloroacetoacetate

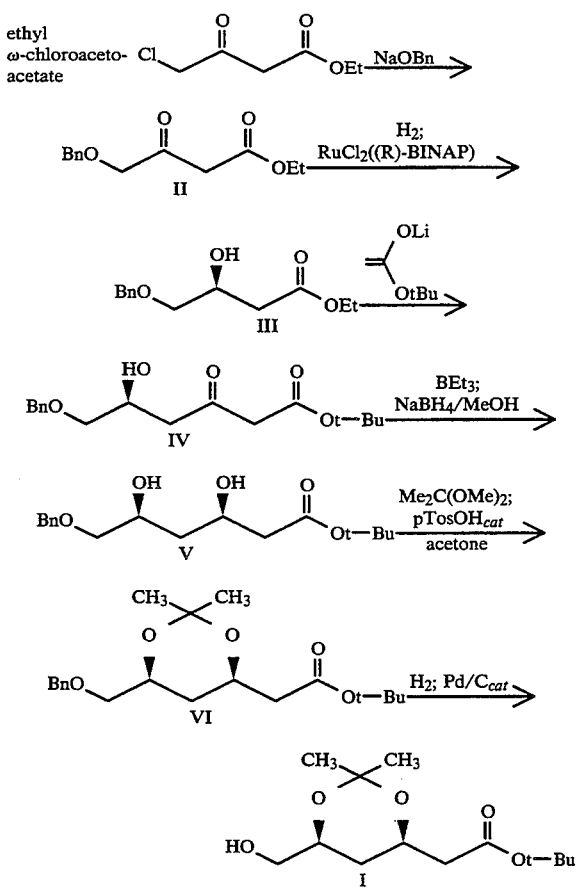

The process according to the invention is expediently carried out as follows. The β-keto ester II is obtained in a known manner from ethyl ω-chloroacetoacetate, and can be purified without difficulty on a multikilogram scale by vacuum distillation on a thin-film evaporator. Asymmetric hydrogenation of compound II yields ethyl 2(S)-hydroxy-3-benzyloxybutyrate of the formula III. The asymmetric hydrogenation is preferably carried out according to the principle of Y. Noyori [M. Kitamura et al., Tetrahadron Lett. 29. 1555 (1988)] with a ruthenium(II)-(R)-BINAP catalyst (BINAP is 2,2'-bis(diphenylphosphino)-1,1'-binaphthyl) using a simplified in-situ preparation of the catalyst [M. Kitamura et al., Tetrahadron Lett. 32, 4163 (1991)]. While the asymmetric hydrogenation on the concrete substrate of the formula II is described in the literature (M. Kitamura et al., J. Am. Chem. Soc. 1988, 110, page 629–631), it is effected therein, with relatively poor enantioselectivity (78% ee) and a relatively poor substrate/catalyst molar ratio (S/C 700/1), at high hydrogen pressure (100 atm) using the catalyst RuBr$_2$[(S)-binap] which, according to footnote 9 (page 630), must be prepared by treating Ru(OCOCH$_3$)$_2$(BINAP), which is difficult to obtain, with two equivalents of HBr. We have significantly improved the enantioselectivity (up to 98% ee), the practicability (use of the readily available in-situ catalyst (in-situ ruthenium(II) chloride-(R)-BINAP catalyst), use of a substantially lower hydrogen pressure (<5 atm H$_2$)) and the economy of this reaction (S:C substantially greater than 1000:1). It is preferably carried out in an autoclave using a polar solvent at elevated temperature and under weak hydrogen pressure, particularly preferably in ethanol at 100° C. under 4 atm hydrogen for 6–12 hours. In the particularly preferred procedure, the solvent is subsequently removed in vacuo and the residue is purified by vacuum distillation on a thin-film evaporator. On the multi-kilogram scale, this reaction can be carried out using a substrate/catalyst molar ratio of up to about 2000:1. The distilled compound of the formula III has a chemical purity of >98% (GC) and an optical purity of 96–98% ee (HPLC analysis on ®Chiralcel OD or $^1$H-NMR analysis using ®Optishift). The yield is 90–97% after distillation. The Claisen condensation of compound III with an excess of the enolate of tert-butyl acetate yields the β-keto-δ-(S)-hydroxy ester of the formula IV. Preferably, 4 equivalents of the enolate are produced by reaction with 4 equivalents of LDA (LDA is lithium diisopropylamide) at −40° C. in THF and then reacted at room temperature with compound III to give compound IV which is crystalline and can be purified on the multikilo scale by recrystallization or, alternatively, via its lithium bromide complex (in analogy with U.S. Pat. No. 4,452,994). The compound of the formula IV, which is obtained in 75–90% yield, has an optical purity of 97.5% ±1% ee (HPLC analysis on Chiralcel OD). The further reaction of the crude, unpurified compound of the formula IV (see examples) also yields an end product of the formula I of high quality.

Within the whole of the synthesis sequence for preparing the structural element of the formula I, no chromatographic purifications of intermediates need be carried out, since the compounds of the formulae II and III can readily be purified by distillation, and the compounds of the formulae IV and (or) V can be readily purified via lithium bromide complexes.

Purified or unpurified product of the formula IV can be reduced with a very high level of diastereoselectivity to give tert-butyl 3(R),5(S)-dihydroxy-6-benzyloxyhexanoate of the formula V. Preferably, this reduction is carried out at a low temperature using sodium borohydride/triethylborane in methanol [in analogy with K. Narasaka, F.-C. Pai, Tetrahedron 40, 2233 (1984)]. The use of this principle for generating the correct relative configuration of HMG-CoA reductase inhibitors is known [EP-A-0319847; F. G. Kathawala et al., Helv. Chim. Acta 69, 803 (1986)]. The two hydroxyl groups of the compound V are protected as an acetonide with the formation of compound VI. Preferably, this reaction is carried out using acetone dimethyl acetal (2,2-dimethoxypropane) with catalysis by p-toluene-sulfonic acid (95–100% yield). The benzyl protective group of compound VI can be removed by means of catalytic hydrogenation (cf. P 4128345.7), preferably in ethyl acetate solution using palladium on charcoal and under about 10 bar of hydrogen. The finished structural element of the formula I can (with losses) be purified by distillation or else by chromatography. After purification, the compound I is obtained in about 70% yield (>95% ee and >99% chemical purity). Consequently, the overall yield of compound of the formula I from commercially available ester of the formula II is about 40% over 5 steps.

The use of compound I for preparing optically pure HMG-CoA reductase inhibitors is described in EP-A-0319847.

The following examples correspond to a preferred embodiment of the novel process. They are not limiting for the process with regard to the reagents, catalysts, solvents, reaction temperatures, pressures, reaction times, and methods for working up, purification and analysis, which are used.

EXAMPLE 1

Ethyl ω-benzyloxyacetoacetate II

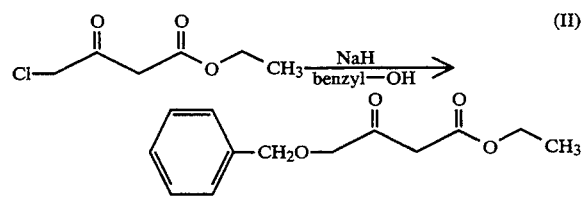

7.35 kg of a 55–60% strength dispersion of NaH are suspended in 101.3 l of toluene. 16.46 l of benzyl alcohol are added dropwise at 20°–25° C. within the space of one hour. The reaction is slightly exothermic (slight cooling with brine). The mixture is subsequently stirred for about 2 hours, at which time no further hydrogen evolution can be observed. 12.5 kg of ethyl chloroacetoacetate are added dropwise, also at 20°–25° C. within the space of 1.5 hours (slightly exothermic, cooling with brine). Thereafter, the mixture is stirred at RT for a further 2 hours. Monitoring with GC indicates complete reaction of the ethyl chloroacetoacetate. The mixture is made slightly acidic (about pH 4) using 75.50 l of 2N citric acid (9.64 kg of citric acid in 67.75 l of water), 10.00 l of toluene are added, and the mixture is extracted with stirring. The aqueous phase is extracted once again with 10.00 l of toluene with stirring. The combined organic phases are dried with sodium sulfate and concentrated on a rotary evaporator. The resulting oil is stirred twice with 2.5 l of n-heptane on each occasion (in order to remove the white oil of the NaH). The oil is separated off. The combined heptane mixtures are left to stand overnight in the stirring vessel, since some more oil separates out. The oil is separated off on the following morning. The whole of the oil is distilled in a two-stage thin-film evaporator at 0.5 mbar, 1st mantle temperature 130° C., 2nd mantle temperature 170° C.

Yield of compound II: 11.83 kg=65.6%, b.p.≈170° C./0.5 torr. Analysis: 25 m "fused silica" OV1 capillary column, injector 250° C. detector 280° C., column temp. 100° C. for 2 min., at 30° C./min. to 140° C., there 6.5 mn. $t_{ret}$: benzyl alcohol 1.2 min., ethyl chloroacetoacetate 2.0 min., compound of the formula II 7.1 min.

EXAMPLE 2

Ethyl 2(S)-hydroxy-3-benzyloxybutyrate III

Asymmetric hydrogenation using a solid in-situ catalyst

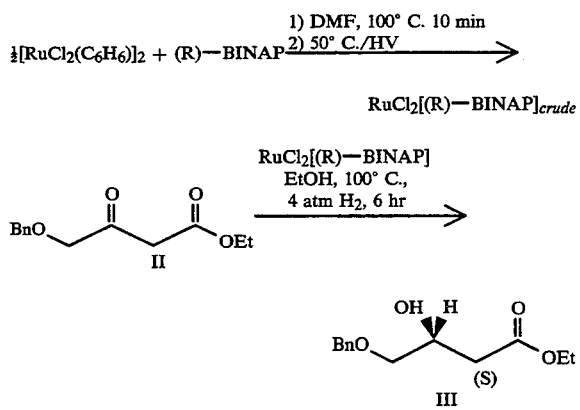

Principle: M. Kitamura et al., Tetrahedron Lett. 29, 1555 (1988); simplified catalyst preparation, M. Kitamura et al., Tetrahedron Lett. 32, 4163 (1991).

a) Preparation of the catalyst

A 10 ml flask was filled with 43.5 mg of benzeneruthenium (II) chloride dimer and 113.7 mg of (R)-BINAP. 3 ml of DMF, through which argon had been bubbled for 5 min, were poured in once the flask had been filled with argon. The resulting solution (suspension according to Kitamura et al.) was heated under argon at 100° C. for 10 min (preheated oil bath). The dark-red solution was cooled and concentrated under pump vacuum, at 50°–70° C., while stirring vigorously (=5 min), and the remaining solid was dried for a further 30 min. under complete high vacuum. It was cooled to RT, gassed with argon and scraped off the wall with a spatula under argon.

b) Preparation of compound III

The solution of 41.1 g of keto ester (from Example 1) in 40.0 ml of abs. ethanol had been bubbled through with argon for 2 hr. in a 250 ml glass insert in a shaking autoclave. 85.0 mg (107 μmol calculated as RuCl2[(R)-BINAP]) of the above catalyst were added. The glass insert was sealed with an argon-filled balloon. The catalyst dissolved completely during agitation. The insert was inserted into a N2-filled autoclave. Remnants of air, N2 and argon were eliminated by threefold injection of 50 atm of H2 and slow pressure release. 2 atm of H2 were then injected. The autoclave was heated to 100° C. The H2 pressure was then adjusted to 4 atm exactly. Shaking took place at 100° C. for 6 hr. The autoclave was left to cool down to RT overnight.

Flushing took place with N2 and the autoclave was opened. The solution was concentrated in a rotary evaporator. A yellow oil was obtained.

GC indicated quantitative conversion of the start. mat. (starting material) into the product of (GC purity crude product 98.5%).

The crude product was fractionated under high vacuum via a ⅜" cm Vigreux column:

---

Frctn. 1   b.p. 80–105° C./0.01 torr; bath 140–150° C.;
1.00 g of colorless oil
Frctn. 2   b.p. 107–112° C./0.01 torr; bath 150° C.;
8.55 g of colorless oil
Frctn. 3   b.p. 114–116° C./0.01 torr; bath 150° C.;
29.20 g of colorless oil
Frctn. 4   b.p. 116–118° C./0.01 torr; bath 150–180° C.
0.62 g of colorless oil
39.37 g of colorless oil
Total yield: 39.37 g (165 mmol) = 95% of theory
GC Analysis:
Frctn. 1: Product purity 77.0% ≈ 16.0% start. mat. → discarded
Frctn. 2: Product purity 95.2% ≈ 1.4% start. mat.
Frctn. 3: Product purity 99.7% ≈ 0% start. mat.
Frctn. 4: Product purity 94.3% ≈ —
Yield of the clean fractions (2–4): 38.37 g (161 mmol) = 92.5% of theory
Optical rotation of frctns. 2 + 3:
59.0 mg/5 ml of abs. non-denatured EtOH, i.e. c = 1.18;
measured: 20° C., D line: −0.105

$$[\alpha]_d^{20} = \frac{-0.105 \times 100}{1.18} = -8.90°$$

Optical purity HPLC: Frctn. 3: 98% ee
Optical purity (Optishift): Frctn. 2: >95% ee

---

EXAMPLE 3

Ethyl 2(S)-hydroxy-3-benzyloxybutyrate III

Asymmetric hydrogenation using an in-situ catalyst in DMF solution

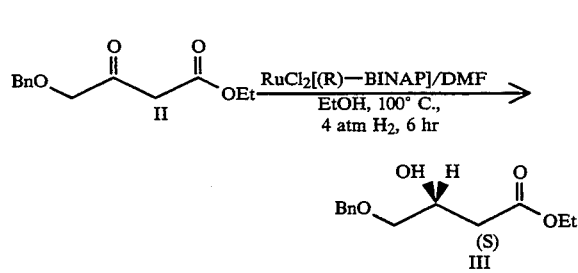

Catalyst preparation and performance of the hydrogenation were effected according to Example 2 with the difference that the DMF solution of the catalyst was not concentrated to dryness but was added as a solution to the ethanolic substrate solution under argon.

The substrate/catalyst ratio was 1000:1.

Hydrogenation took place for 6 hr. at 100° C./4 atm H2 pressure.

The crude product was fractionated under high vacuum:

---

Frctn. 1 90–110° C./≈ 0.01 torr 0.83 g of colorless oil - discarded
Frctn. 2 111–120° C./≈ 0.01 torr 11.84 g of colorless oil - purity (GC): 98.0%
Frctn. 3 123–125° C/≈ 0.01 torr 27.74 g of colorless oil - purity (GC): 97.9%
Yield of the clean fractions (2 + 3): 39.58 g (166 mmol) = 95.4% of theory;
Purity: 98%
Optical rotation of frctns. 2 + 3: 58.9 mg/5 ml of abs. non-denatured EtOH, i.e. c = 1.178;
measured: 20° C., D line: −0.107

-continued $$[\alpha]_D^{20} = \frac{-1.107 \times 100}{1.178} = -9.083°$$

Optical purity (Optishift): Frctn. 2: >95% ee.

EXAMPLE 4

Ethyl 2(S)-hydroxy-3-benzyloxybutyrate III.

Asymmetric hydrogenation using an in-situ catalyst in DMF solution

| Materials: | |
|---|---|
| 10 kg | keto ester II |
| 18.0 g | (R)-(+)-BINAP |
| 7.0 g | benzeneruthenium(II) chloride dimer |
| 10 l | abs. ethanol, denatured with toluene |
| 900 ml | N,N-dimethylformamide |

2.0 l of N,N-dimethylformamide are freshly distilled off under high vacuum from 4 A molecular sieves, a middle fraction (b.p. 35°–40° C.) being collected. 900 ml of freshly distilled N,N-dimethylformamide are initially introduced into a two-liter flask having a stirring magnet, argon feed-line and bubble counter, and argon is bubbled through. 18.0 g of (R)-(+)-BINAP and 7.0 g of benzeneruthenium(II) chloride dimer are added. The resulting solution is bubbled-through with argon for 15 minutes and then immersed deeply for 10 minutes into an oil bath which has been preheated to 100° C., with the argon being allowed to continue to bubble through the solution. The resulting clear, dark-red-brown solution is allowed to cool down to room temperature under argon. In the meantime, 10 l of abs. ethanol (denatured with toluene) and 10 kg of keto ester II (from Example 1) are charged into a 30 l steel autoclave. A vigorous stream of argon is bubbled through the solution. The catalyst solution is transferred under pressure to the substrate solution with argon using a double cannula.

The autoclave is sealed and then flushed with hydrogen. 2 bar of hydrogen are injected and the autoclave is then heated to 100° C. Once this temperature has been reached, the hydrogen pressure is adjusted to 4 bar exactly, and stirring takes place under these conditions for 12 hours. The autoclave is allowed to cool down. Using GC analysis, a sample which is withdrawn indicates >99% hydrogenation. HPLC analysis on ⓡChiralcel OD indicates 97.4% ee of the crude product. The autoclave is flushed with nitrogen, the contents are withdrawn, and the ethanol is removed in vacuo. Subsequently, the DMF is removed under high vacuum at a bath temperature of 60° C. The residue is distilled on a thin-film evaporator (140°–150° C. mantle temperature, 0.1 torr). 9.70 kg (96.2% of theory) of a pale-yellow (almost colorless) oil are obtained, GC purity: >98%, optical purity (ⓡChiralcel OD): 97.1%, $[\alpha]_D^{20} = -8.3°$ (c=1.2, in abs ethanol)

(R)-(+)-BINAP can be recovered from the distillation bottom (black viscous oil).

EXAMPLE 5 tert-Butyl 3-oxo-5(S)-hydroxy-6-benzyloxyhexanoate IV

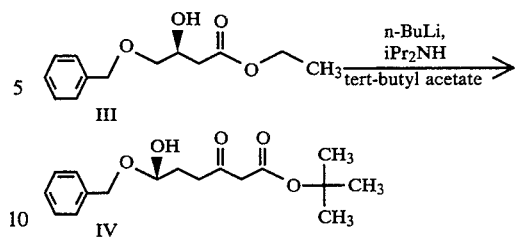

Materials:
9.4 l (66 mol) diisopropylamine
13.4 l THF (abs. according to Karl Fischer)
43.6 l=29.65 kg (69.76 mol) n-BuLi (15% strength in hexane)
9.0 l (67.6 mol) tert-butyl acetate
4 kg (6.30 mol) compound III (from Example 2, 3 or 4)
32 l toluene 9.4 l of diisopropylamine are dissolved in 9.4 l of abs. THF and 29.65 kg of n-BuLi are added dropwise at 0° C. The mixture is subsequently stirred at room temperature for 30 minutes and then cooled to −40° C. 9 l of tert-butyl acetate are added dropwise at this temperature. The mixture is subsequently stirred at −40° C. for 1 hour. Then, 4 kg of compound III, dissolved in 4 l of THF, are added dropwise. The mixture is subsequently stirred at −40° C. for 2 hours. After that, 7.4 l of water are added without further cooling, and the mixture is then stirred for 10 minutes. Subsequently, the mixture is extracted twice with 16 l of toluene on each occasion. The combined toluene-hexane phases are dried and concentrated on a rotary evaporator. The product becomes semi-solid on the rotary evaporator. Yield: 8.0 kg=155.7% of compound IV.

EXAMPLE 6

Option of purifying the keto ester IV from Example 5 via a lithium bromide complex 62 g of the crude product from Example 5 are dissolved in 260 ml of petroleum ether (40°–80° C.) (if necessary, then add toluene dropwise until a clear solution is obtained). 55 g of anhydrous lithium bromide are added, and the suspension is then stirred for one hour with the exclusion of moisture. The lithium bromide complex is filtered off with suction and washed with 50 ml of petroleum ether. The crystals are introduced into 100 ml of water and 250 ml of methyl tert-butyl ether, and the mixture is stirred vigorously for 30 minutes. The organic phase is separated off and the solvent is removed in vacuo, and the oily residue is taken up in 100 ml of diisopropyl ether. In doing this, crystallization commences. The solid is filtered off with suction, washed with 20 ml of diisopropyl ether, and dried in vacuo. 29 g (82% of theory based on β-hydroxy ester III) are obtained of colorless solid IV which, in contrast to the crude product, is present almost completely in the enol form (¹H-NMR), melting point 136° C.

EXAMPLE 7 tert-Butyl 3(R),5(S)-dihydroxy-6-benzyloxyhexanoate V

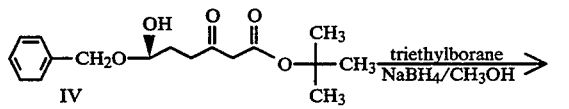

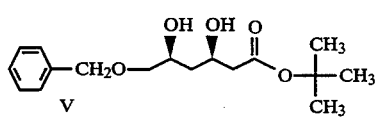

ice cooling (duration about 1 hour). Once addition is complete, the mixture is treated with THF. The aqueous phase is separated off and extracted by stirring twice with 13 l of toluene on each occasion and once with 13 l of ethyl acetate. The resulting organic phase is concentrated on a rotary evaporator. Yield: 2.20 kg=122.6% of pale yellow oil (compound V).

EXAMPLE 8 tert-Butyl (3R,5S)-6-benzyloxy-3,5-O-isopropylidene-3,5-dihydroxyhexanoate VI

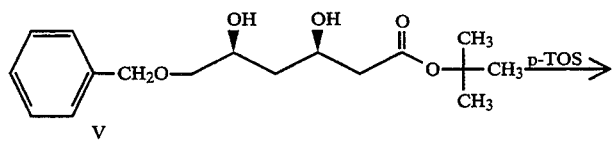

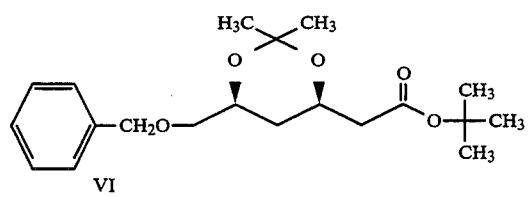

Materials:
2.77 kg (100% =1.94 kg =6.29 mol) compound IV (Example 5)
24.5 l THF
13.3 l triethylborane, 1 molar in hexane
680.9 g sodium borohydride
17.5 l methanol
13.75 l hydrogen peroxide 2.77 kg of compound IV are dissolved in 24.5 l of THF at 20°–25° C. 13.3 l of triethylborane are allowed to run in relatively quickly at the same temperature. The reaction is endothermic. The mixture is subsequently stirred at 20°–25° C. for 10 minutes and then cooled to −60° C. 680.9 g of sodium borohydride are added at this temperature. This addition is also not associated with any exothermic reaction. Immediately thereafter, the dropwise addition of 11.5 l of methanol is begun (duration about 1.5–2 hours, exothermic reaction up to max. −60° C.). Once addition is complete, the mixture is subsequently stirred at −60° C. for 2 hours. After about 1.5 hours (monitoring with TLC), the mixture is taken out of the reactor and added to the feed vessels. 13.75 l of 35% strength hydrogen peroxide are added, together with 13.75 l of water and 6 l of methanol, to the cold reactor, and the mixture is metered in, with stirring and cooling, at initially 0° C. to max 15° C., from the feed vessels in association with complete dry- Materials:
2.2 kg (7.087 mol) "diol" (compound V from Example 7)
30 l acetone
1.506 kg (14.17 mol) 2,2-dimethoxypropane
0.135 kg (0.708 mol) p-toluenesulfonic acid
5 l ethyl acetate 2.2 kg of compound V are dissolved at room temperature in 30 l of acetone. At temperatures of 20° to 25° C., 1.506 kg of 98% strength 2,2-dimethoxypropane (=1.778 l) and, subsequently, 0.135 kg of p-toluenesulfonic acid hydrate are added, and the mixture is subsequently stirred at these temperatures for 3 hours. The original colorless solution turns slowly yellowish after 1–2 hours. The mixture is left to stand at 25° C. overnight. It is concentrated in vacuo on the following morning, and the residue (oil) is dissolved in 5 l of ethyl acetate. The organic phase is then washed once with 2.5 l of saturated NaHCO$_3$ solution and once with 2.5 l of saturated NaCl solution. It is then dried over Na$_2$SO$_4$, clarified and concentrated in vacuo. Crude yield: 2.38 kg (96% of theory) of oil.

EXAMPLE 9 tert-Butyl (3R,5S)-6-hydroxy-3,5-O-isopropylidene-3,5-dihydroxyhexanoate (I)

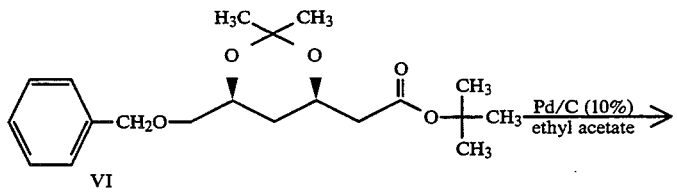

-continued

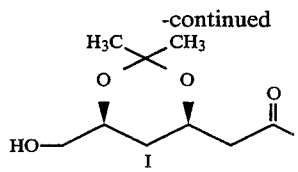

Materials:
2.38 kg (6.79 mol) compound VI from Example 8
30 l ethyl acetate
0.238 kg Pd/C (10%)

2.38 kg of compound VI are dissolved in 30 l of ethyl acetate. 0.238 kg of Pd/C (10% strength) is added under $N_2$, and hydrogenation takes place at 10 bar $H_2$ for 8 hours in a stirring autoclave. On the following morning, the reaction is checked by TLC. If the reaction is still not finished, filtration with suction takes place, new catalyst is added and the hydrogenation is continued. If the hydrogenation is complete, the mixture is filtered off from the catalyst with suction and concentrated on a rotary evaporator. Crude yield: 1.55 kg (87.9% of theory, oil). The resulting oil is purified in two chromatography columns. For this, 8 kg of crude oil, together with 8 l of MTB ether (methyl tert-butyl ether)/cyclohexane 1:1, are adsorbed onto a 15 kg silica gel column which has been flooded with MTB ether/cyclohexane 1:1, and eluted with the same running mixture. The first eluate of 50 l is discarded. After that, 20 fractions of 5 l each are taken off and checked using TLC. The product fractions are concentrated on a rotary evaporator.

Yield: 600 g of compound I (starting from the ester condensation, i.e. starting from Example 5, a yield of 43.6% consequently results over 4 steps).

We claim:

1. A process for preparing tert-butyl (3R, 5S)-6-hydroxy-3,5-O-isopropylidene-3,5-dihydroxyhexanoate of the formula I,

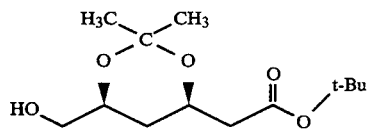

wherein ethyl ω-benzyloxyacetoacetate of the formula II

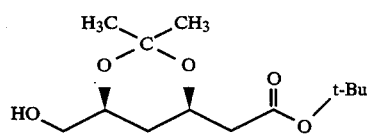

wherein Bn is benzyl is asymmetrically hydrogenated to give ethyl 2(S)-hydroxy-3-benzyloxybutyrate of the formula III,

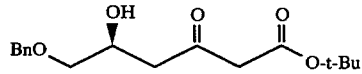

the β-hydroxy ester of the formula III is converted by means of a Claisen condensation with

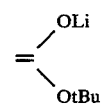

into the β-keto-σ-(S)-hydroxy ester of the formula IV,

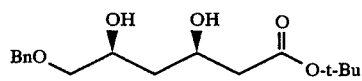

the resultant ester of the formula IV is converted by diastereoselective reduction into tert-butyl 3(R), 5(S)-dihydroxy-6-benzyloxyhexanoate of the formula V,

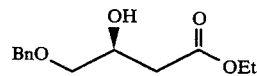

the hydroxyl groups in the dihydroxy ester of the formula V are protected, with the formation of the acetonide of the formula VI,

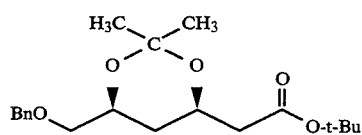

and the benzyl protective group is removed from the acetonide of the formula VI, with the formation of the compound of the formula I;
wherein the asymmetric hydrogenation of compound II to give compound III is carried out
a) at a substrate/catalyst molar ratio substantially greater than 1000:1,
b) using an in-situ ruthenium(II) chloride-(R)-BINAP catalyst, and
c) under a hydrogen pressure of less than 5 atm $H_2$.

2. The process as claimed in claim 1, wherein the compound I is obtained at high chemical and optical purity without having to subject intermediate stages to chromatography.

* * * * *

UNITED STATES PATENT AND TRADEMARK OFFICE
CERTIFICATE OF CORRECTION

PATENT NO. : 5,399,722

DATED : March 21, 1995

INVENTOR(S): Gerhard BECK et. al.

It is certified that error appears in the above-indentified patent and that said Letters Patent is hereby corrected as shown below:

Claim 1, column 11, lines 43-49, formula I,

" 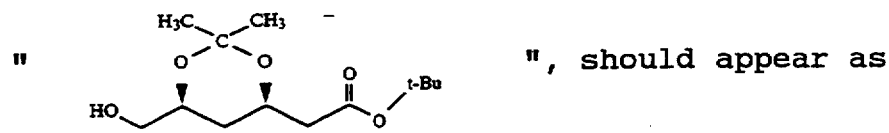 ", should appear as

-- 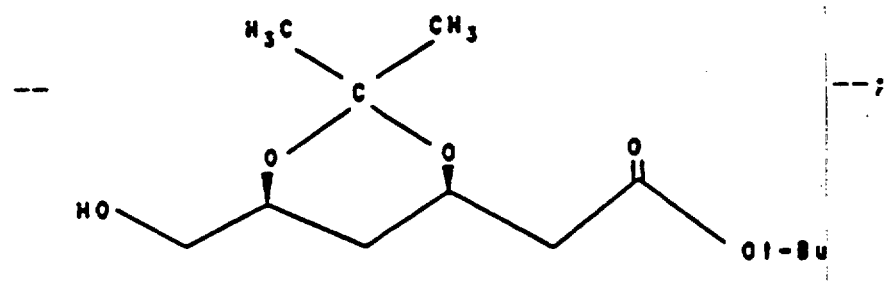 --;

Claim 1, column 11, lines 52-58, delete the formula,

" 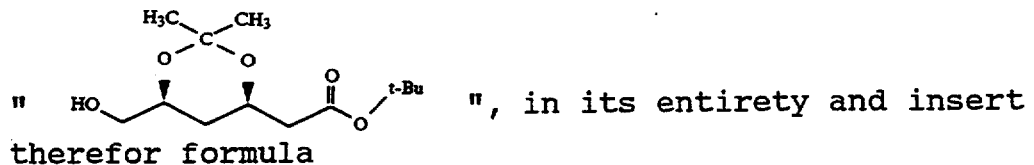 ", in its entirety and insert therefor formula

-- 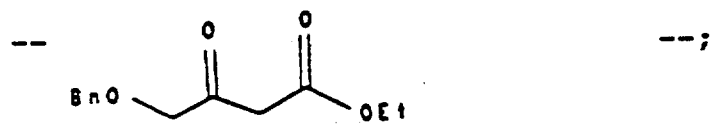 --;

UNITED STATES PATENT AND TRADEMARK OFFICE
CERTIFICATE OF CORRECTION

PATENT NO. : 5,399,722
DATED : March 21, 1995
INVENTOR(S) : Gerhard BECK et al.

It is certified that error appears in the above-indentified patent and that said Letters Patent is hereby corrected as shown below:

Claim 1, Column 11, line 59, after "benzyl", insert --and--.

Signed and Sealed this

Twenty-seventh Day of June, 1995

Attest:

BRUCE LEHMAN

*Attesting Officer*  Commissioner of Patents and Trademarks